United States Patent
Namikawa et al.

(10) Patent No.: US 9,021,899 B2
(45) Date of Patent: May 5, 2015

(54) LIQUID FEEDING DEVICE USING BALL SCREW, AND ANALYZER

(75) Inventors: Nobuhiro Namikawa, Kyoto (JP); Takeaki Inoue, Kyoto (JP); Akioki Nakamori, Kyoto (JP); Shinsuke Inoue, Kyoto (JP); Yasuhiro Takayama, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 299 days.

(21) Appl. No.: 13/423,687

(22) Filed: Mar. 19, 2012

(65) Prior Publication Data

US 2013/0239705 A1    Sep. 19, 2013

(51) Int. Cl.
 *G01N 1/14* (2006.01)
 *G01N 33/18* (2006.01)

(52) U.S. Cl.
 CPC .......... *G01N 1/14* (2013.01); *G01N 2001/1427* (2013.01); *G01N 33/1846* (2013.01)

(58) Field of Classification Search
 CPC .......... G01N 1/10; G01N 1/14; G01N 30/16; G01N 30/18; G01N 30/24; B01L 3/0227; B01L 3/0234
 USPC ............... 73/863.01, 863.02, 863.03, 863.21, 73/863.22, 864.81, 864.83, 864.85, 864.87
 See application file for complete search history.

(56) References Cited

U.S. PATENT DOCUMENTS

| | | | | |
|---|---|---|---|---|
| 5,526,255 A | * | 6/1996 | Shenk | 700/56 |
| 6,715,506 B1 | * | 4/2004 | Ikushima | 137/14 |
| 7,284,453 B2 | * | 10/2007 | Li et al. | 73/863.01 |
| 7,585,468 B2 | * | 9/2009 | Jaghuber | 422/561 |
| 2009/0016931 A1 | * | 1/2009 | Seino et al. | 422/63 |
| 2012/0039750 A1 | * | 2/2012 | Yahata | 422/80 |

FOREIGN PATENT DOCUMENTS

| | | | |
|---|---|---|---|
| JP | 62-226060 | 10/1987 | |
| JP | 01-097546 | 4/1989 | |
| JP | 4-133053 | 12/1992 | |
| JP | 07-319990 | 8/1995 | |
| JP | 2006-047323 A | 2/2006 | |
| JP | 2006-084307 A | 3/2006 | |
| WO | 2008/047405 A1 | 4/2008 | |
| WO | WO2010/122655 A1 * | 10/2010 | G01N 27/06 |

OTHER PUBLICATIONS

Office Action dated Sep. 18, 2012 in corresponding Japanese Patent Application No. 2009-216335.

* cited by examiner

*Primary Examiner* — Randy W Gibson
*Assistant Examiner* — Natalie Huls
(74) *Attorney, Agent, or Firm* — Sughrue Mion, PLLC

(57) ABSTRACT

A control device controls driving of a pulse motor to cause liquid that is sucked into a syringe in a single suction process to be discharged over a plurality of discharge processes. The control method of the control device is a method that controls driving of the pulse motor so that rotation of a ball screw for executing each discharge process starts from an identical rotational angle position relative to a slit of a coupling.

4 Claims, 3 Drawing Sheets

US 9,021,899 B2

LIQUID FEEDING DEVICE USING BALL SCREW, AND ANALYZER

TECHNICAL FIELD

The present invention relates to a liquid feeding device that drives a syringe using a ball screw (including a trapezoidal screw), and an analyzer such as a total organic carbon (TOC) measurement instrument that includes the liquid feeding device as a liquid feeding device for feeding a sample liquid or the like.

BACKGROUND ART

TOC measurement of organic matter included in sample water containing few impurities, such as water for manufacturing pharmaceuticals, process water for semiconductor manufacturing, cooling water, boiler water, or tap water, is performed for the purpose of managing such kinds of water.

A instrument that measures a TOC concentration of sample water while keeping the sample water in the liquid phase has also been developed as a TOC measurement instrument. In the case of such a TOC measurement instrument, while keeping sample water in the liquid phase, organic matter contained in the sample water is oxidized to carbon dioxide by being subjected to ultraviolet light irradiation at an oxidative decomposition unit, and thereafter is introduced into a carbon dioxide separation unit. At the carbon dioxide separation unit, a sample water channel and a measurement water channel, through which measurement water flows, are brought into contact through a gas permeable membrane, and thus carbon dioxide contained in the sample water is transferred to measurement water. The measurement water into which carbon dioxide has been transferred is sent to a conductivity measuring unit to measure the conductivity thereof. By previously determining a calibration curve representing the relationship between the conductivity of measurement water and the carbon dioxide concentration of sample water, it is possible to determine the carbon dioxide concentration of the sample water based on the measured conductivity of the measurement water (see Patent Literature 1).

In the case of such a TOC measurement instrument, a liquid feeding device that drives a syringe using a ball screw is used as a liquid feeding device for feeding sample water. Further, in some cases a liquid feeding device that drives a syringe using a ball screw is also used as a liquid feeding device that supplies measurement water to the conductivity measuring unit. In a liquid feeding device of this kind, a ball screw is used as a linear feed mechanism. Rotation of the ball screw is driven by a pulse motor to thereby control the flow rate for injecting sample water or feeding measurement water. In this connection, in some cases feeding of liquid is controlled by means of the flow velocity instead of the flow rate. Although control of liquid feeding by means of the flow rate is described hereunder, the present invention also includes a case in which liquid feeding is controlled by means of the flow velocity instead of the flow rate.

CITATION LIST

Patent Literature

[Patent Literature 1] International Publication No. WO 2008/047405

SUMMARY OF INVENTION

Problems to be Solved by the Invention

In a case where a ball screw is used as a power mechanism, when a feed length per rotational angle of the ball screw is measured, as shown in FIG. 2, it is found that the feed length per rotational angle includes an error. The vertical axis in FIG. 2 represents measurement results for a feed length of a ball screw per unit time when the ball screw is rotated at a constant speed. The horizontal axis represents the number of data that is sent to a pulse motor driving circuit from a control device to send a pulse signal to a pulse motor that rotates the ball screw, and by sending the data at regular intervals, the pulse motor is caused to rotate at a constant speed. Since the ball screw is rotated at a constant speed, the feed length represented by the vertical axis is also a feed length per fixed rotational angle of the ball screw. It is thus found that a variable error for a single rotation of the ball screw varies with periodicity as in a sine curve.

In the case of a TOC measurement instrument that measures a TOC concentration by treating sample water while keeping the sample water in the liquid phase and measuring the conductivity thereof, the flow rate of the sample water is controlled to a very low flow rate of 100 to 500 µL/min and measurement is performed. A conductivity that is measured at a very low flow rate of this kind varies depending on the flow rate of the sample water or measurement water. When a ball screw is used as a driving source of a syringe that feeds a liquid, a feed error of the ball screw becomes, as it is, a variation in the flow rate of the sample water or measurement water, and is manifested as an error in a conductivity measurement value.

The occurrence of a variable error in the feed length of a ball screw is ascribable to the machining accuracy of the ball screw itself as well as the machining accuracy of support mechanisms such as guides or nuts for making the ball screw serve as a linear feed mechanism. Therefore, to reduce feed errors in a liquid feeding device that uses a ball screw as a linear feed mechanism, it is necessary to increase the machining accuracy of not just the ball screw, but also of mechanical components that also include support mechanisms such as guides and nuts. However, the greater the attempt that is made to increase the machining accuracy of all mechanical components including the ball screw, the greater the resulting increase in costs and in the difficulty of the processing techniques.

Thus, an object of the present invention is not to reduce variable errors in the feed length of a ball screw by solely increasing the machining accuracy, but rather is to improve a method of using a ball screw and as a result reduce the influence of a ball screw on measurement results such as conductivity measurement values, even in the case of a ball screw having a variable error as shown in FIG. 2.

Means for Solving the Problems

According to the present invention, when using a ball screw as a driving source of a syringe that feeds liquid, and discharging the liquid from the syringe a plurality of times during a single stroke from an upper end to a lower end of the ball screw, the cycles of the plurality of discharge operations are uniformized by detecting a rotation of the ball screw with a sensor and controlling the rotation.

More specifically, a liquid feeding device of the present invention includes a syringe, a syringe support unit including a ball screw that drives the syringe, a pulse motor that rotates the ball screw, a rotation detection mechanism that detects a rotation of the ball screw, and a control device that controls driving of the pulse motor.

The syringe includes a cylinder, and has a piston that is capable of sliding in the cylinder, and a liquid inlet/outlet port at a distal end of the cylinder, wherein a piston rod that is integrated with the piston protrudes to a proximal end side of the cylinder, and the syringe performs suction and discharge of liquid from the inlet/outlet port by causing the piston to slide through the piston rod.

The syringe support unit includes a piston rod support body that is attached to the piston rod of the syringe, and a ball screw that is screwed together with the piston rod support body, and the syringe support unit uses the ball screw as a linear feed mechanism to move the piston rod support body by rotation of the ball screw.

The rotation detection mechanism includes a coupling and a photo sensor. The coupling is formed in a disk shape and has a slit in a radial direction, and is attached integrally with the ball screw so as to rotate together with the ball screw. The photo sensor is combined with the coupling so as to detect a position of the slit of the coupling.

The control device that controls driving of the pulse motor is a device that controls operations of the syringe so that liquid that is sucked into the syringe in a single suction process is discharged over a plurality of discharge processes, and as the control method thereof, the control device controls driving of the pulse motor so that rotation of the ball screw for executing each discharge process starts from an identical rotational angle position relative to the slit of the coupling.

The rotation starting positions of the ball screw in the respective discharge processes from the syringe are uniformized to make the rotational cycle of the ball screw uniform in the respective discharge processes. Therefore, after one discharge process ends, before beginning the next discharge process the ball screw is rotated as far as the same rotational phase of the ball screw as that at the time of starting the previous discharge process, and thus each discharge process is executed with the rotational phase of the ball screw in a uniform state. If by chance the rotational position of the ball screw when a discharge process ends matches the rotational position when the discharge process started, the next ball screw rotation can be started from the stopped position. Thus, even if a ball screw has a feed error as shown in FIG. 2, the liquid feed flow rate is constant in the respective discharge processes.

A TOC measurement instrument according to the present invention includes: a sample supply unit including a liquid feeding device that collects and supplies sample water; an oxidative decomposition unit that is connected to the sample supply unit and that oxidizes organic matter contained in the sample water supplied from the sample supply unit to carbon dioxide; a carbon dioxide separation unit that includes a sample water channel through which the sample water that has passed through the oxidative decomposition unit flows, and a measurement water channel through which measurement water consisting of deionized water flows, wherein a gas permeable membrane is interposed between the sample water channel and the measurement water channel to enable transfer of carbon dioxide therethrough; and a conductivity measuring unit that measures a conductivity of the measurement water from the carbon dioxide separation unit. The TOC measurement instrument uses the liquid feeding device of the present invention as the liquid feeding device of the sample supply unit.

Advantageous Effects of Invention

The liquid feeding device of the present invention is configured so that, when discharging liquid by performing a plurality of discharge processes during one stroke of a ball screw that is a driving source of a syringe, rotation of the ball screw in the respective discharge processes starts from an identical rotational angle position, and therefore variations in the discharge amounts that are caused by a feed error of the ball screw can be suppressed.

In the case of a TOC measurement instrument, as the result of performing feed error control according to the present invention on a sample for which there was a possibility of the measurement accuracy with respect to 0.5 mgC/L thereof (a carbon concentration of 0.5 mg/L is expressed as 0.5 mgC/L; 0.5 mgC/L=0.5 ppmC) varying by approximately ±20 μgC/L, it was possible to reduce the measurement accuracy to ±1 μgC/L.

MODE FOR CARRYING OUT THE INVENTION

Figure 1:
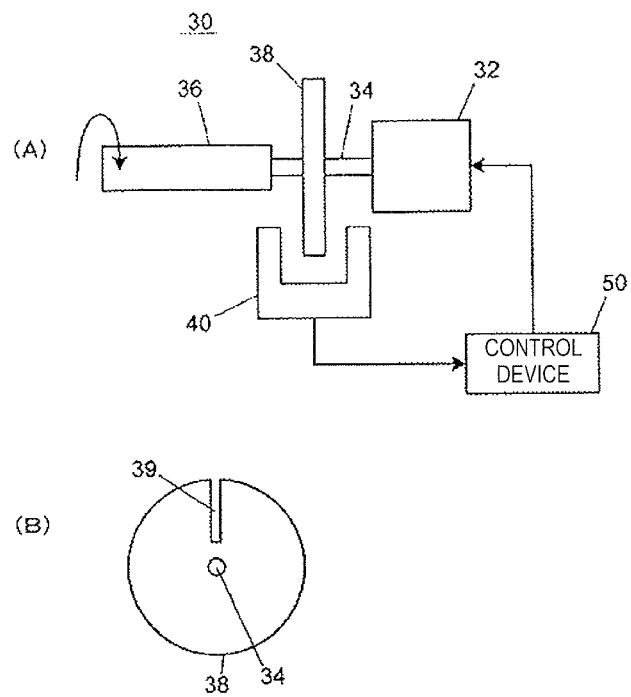
FIG. 1 illustrates a syringe driving mechanism in a liquid feeding device according to one embodiment, in which (A) is a schematic front view, and (B) is a plan view illustrating an example of a coupling that is used therein.

A syringe driving mechanism in a liquid feeding device according to one embodiment is shown in FIG. 1.

A syringe driving mechanism 30 includes a ball screw 36 that moves a piston rod of a syringe, a pulse motor 32 that rotates the ball screw 36, a coupling 38 and a photo sensor 40 as a rotation detection mechanism, and a control device 50. The coupling 38 is formed in a disk shape and has a slit 39 in a radial direction thereof, and is attached integrally with the ball screw 36 so as to rotate together with the ball screw 36. In this case, the coupling 38 is fixed to a rotating shaft 34 of the pulse motor 32 that rotates the ball screw 36, so that the rotating shaft 34 passes through the center of the coupling 38. A photocoupler is used as one example of the photo sensor 40, and is combined with the coupling 38 so as to detect the position of the slit 39 of the coupling 38. The slit 39 has a length of approximately 15 mm and a width of 1.2 mm. A rotational position of the ball screw 36 can be recognized by detecting the position of the slit 39.

The control device 50 controls driving of the pulse motor 32 so as to cause liquid that is sucked into the syringe in a single suction process to be discharged over a plurality of discharge processes. The control method of the control device 50 is a method that controls driving of the pulse motor 32 so that rotation of the ball screw 36 for executing the respective discharge processes starts from an identical rotational angle position relative to the slit 39 of the coupling 38. The control device 50 may be implemented by a dedicated computer (CPU) for the liquid feeding device, may be implemented by a computer that also serves as a control device of the TOC measurement instrument in which the liquid feeding device is used, or may be implemented by a general-purpose personal computer.

In the syringe driving mechanism 30, the coupling 38 in which the slit 39 is formed rotates together with rotation of the ball screw 36. The photo sensor 40 has an optical path where light passes along at all times. By inserting the coupling 38, in which the slit 39 is formed, so as to cross the optical path of the photo sensor 40, and rotating the coupling 38, at a portion of the coupling 38 without the slit 39, the photo sensor 40 enters a light-shielded state, while at a portion of the coupling 38 with the slit 39, a state is entered in which light is transmitted to the photo sensor 40. The rotational position of the ball screw 36 can be detected by electrical signals that are based on whether light is shielded from or transmitted to the photo sensor 40 being recognized by the control device 50.

Figure 3:
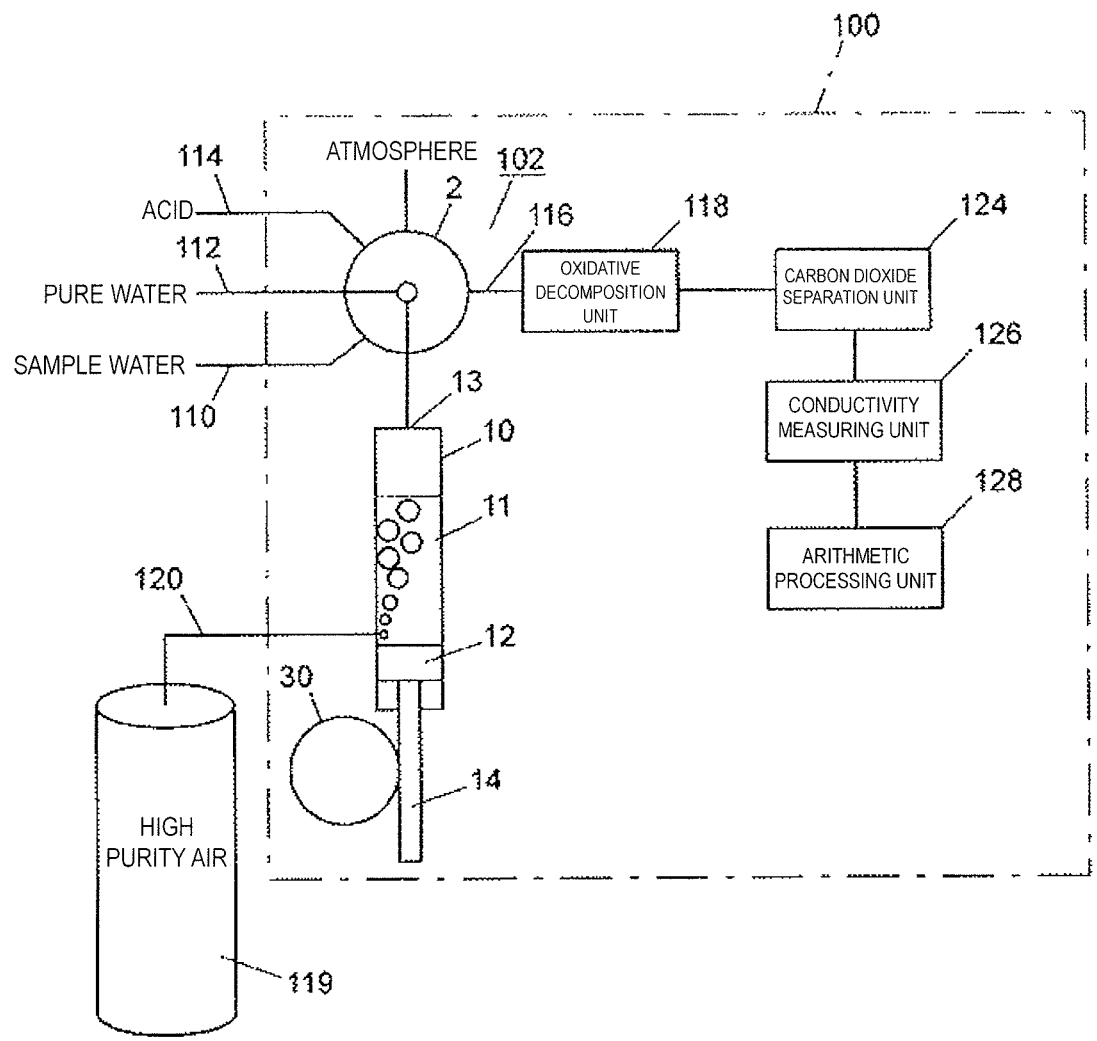
FIG. 3 is a schematic configuration diagram illustrating a TOC measurement instrument according to one embodiment.

An embodiment of a TOC measurement instrument that uses the above-described liquid feeding device is shown in FIG. 3.

In a TOC measurement instrument 100, a liquid feeding device 102 is provided as a sample collection device. The liquid feeding device 102 includes an 8-port valve 2 that is a channel switching valve, and a syringe 10 for water sampling that is connected to a common port of the valve 2. A gas supply channel 120 through which a gas that does not contain carbon dioxide is supplied into the syringe 10 is connected to the syringe 10.

A channel 110 is connected to one of the ports of the valve 2 to receive sample water from outside the housing of the TOC measurement instrument. A channel 112 is connected to another of the ports of the valve 2 to receive pure water from outside the housing. A channel 114 is connected to yet another of the ports of the valve 2 to receive an acid for acidifying sample water or pure water collected in the syringe 10 from outside the housing. A channel 116 that is connected to an oxidative decomposition unit 118 is connected to yet another of the ports of the valve 2. Another of the ports of the valve 2 is configured to be capable of opening to the atmosphere.

An inorganic acid such as hydrochloric acid, sulfuric acid, or phosphoric acid is used as the acid. The pH of sample water or pure water contained in the syringe 10 is preferably adjusted to, for example, 4 or less by adding the acid.

The valve 2 is constituted by a stator provided with a plurality of ports, and switching occurs by rotating a rotor so that the syringe 10 connected to the common port can be in communication with any one of the ports.

Sample water or pure water and, in addition, an acid can be introduced into the syringe 10 by sliding a piston 12 in a vertical direction while keeping the inside of a cylinder of the syringe 10 in a liquid-tight state. The sample water or pure water collected in the syringe 10 can be supplied to the oxidative decomposition unit 118 from the channel 116 through the valve 2 by pushing the piston upward. The piston 12 is attached to the distal end of a piston rod 14. The piston 12 slides in a vertical direction inside the cylinder as a result of the piston rod 14 being driven by the syringe driving mechanism 30 shown in FIG. 1 that adopts a pulse motor as a driving source.

The gas supply channel 120 is connected to a lower end portion of a cylinder 11 of the syringe 10 to supply a gas that does not contain carbon dioxide into the syringe 10 for aeration treatment. The position at which the gas supply channel 120 is connected to the cylinder 11 is above the piston 12 in a state in which the piston 12 has moved to the lower end of the cylinder 11. Examples of the gas that does not contain carbon dioxide include, but are not limited to, high purity air contained in a gas canister 119 and high purity air supplied through a column filled with a filler that adsorbs carbon dioxide.

The oxidative decomposition unit 118 is a unit at which, while sample water or pure water (hereinafter, it is assumed that pure water is also included when only the term "sample water" is used) is flowing through a channel thereof, the sample water is irradiated with ultraviolet light to decompose organic matter contained in the sample water by oxidation to carbon dioxide.

The sample water that has passed through the oxidative decomposition unit 118 is introduced into a carbon dioxide separation unit 124. In the carbon dioxide separation unit 124, a carbon dioxide component contained in the sample water is transferred to measurement water through a gas permeable membrane. The sample water that has passed through the carbon dioxide separation unit 124 is disposed of.

The measurement water that has passed through the carbon dioxide separation unit 124 is introduced into a conductivity measuring unit 126. The conductivity measuring unit 126 is provided with an electrode that contacts the measurement water, and the conductivity of the measurement water is detected by the electrode. Pure water such as deionized water that has been purified with an ion exchange resin is used as the measurement water. The conductivity of the measurement water varies depending on the concentration of the carbon dioxide component transferred from the sample water to the measurement water in the carbon dioxide separation unit 124, and therefore the concentration of the carbon dioxide component of the sample water can be determined based on the conductivity detection value of the measurement water. The carbon dioxide component is a component that is generated as the result of a TOC component contained in the sample water being subjected to oxidative decomposition at the oxidative decomposition unit 118, and thus the TOC concentration of the sample water can be determined.

An arithmetic processing unit 128 is connected to the electrode for conductivity measurement of the conductivity measuring unit 126 to calculate the TOC concentration of sample water based on a conductivity detected by the conductivity measuring unit 126.

In this TOC measurement instrument, the valve 2 is set so that the channel 112 for receiving pure water is connected to the syringe 10 when performing a blank measurement, and is set so that the channel 110 for receiving sample water is connected to the syringe 10 when performing a sample measurement, to thereby collect pure water or sample water of an appropriate amount, for example, 3 ml, in the syringe 10. Furthermore, the valve 2 is switched so that the syringe 10 is connected to the port connected to the channel 114 for supplying an acid, and a predetermined amount of acid is sucked into the syringe 10 by further withdrawing the piston 12 of the syringe to adjust the pH of the pure water or sample water to 4 or less. Thereafter, in a state in which the valve 2 has been switched so as to connect the syringe 10 to the port opened to the atmosphere, the piston 12 is withdrawn as far as the lower end of the cylinder. In this state, high purity air is supplied to the syringe 10 from the channel 120 at a flow velocity of, for example, 100 ml/min for 90 seconds to subject the pure water or sample water collected in the syringe 10 to aeration treatment so that inorganic carbon included in the pure water or the sample water is removed therefrom and released into the atmosphere.

After the completion of the aeration treatment, the valve 2 is switched so as to connect the syringe 10 to the channel 116 to supply the pure water or sample water contained in the syringe 10 to the oxidative decomposition unit 118. The pure water or sample water contained in the syringe 10 is supplied to the oxidative decomposition unit 118 over a plurality of discharge processes, and rotation of the pulse motor is controlled so as to start rotation of the ball screw in the syringe driving mechanism 30 from an identical rotational position in each discharge process. In the oxidative decomposition unit 118, organic carbon contained in the pure water or sample water is oxidized and decomposed to carbon dioxide by irradiation with ultraviolet light from an ultraviolet lamp. The pure water or sample water that has passed through the oxidative decomposition unit 118 is sent to the carbon dioxide separation unit 124. In the carbon dioxide separation unit 124, the pure water or sample water is brought into contact with measurement water through a gas permeable membrane so that carbon dioxide is transferred to the measurement water, and the conductivity of the measurement water is then detected by the conductivity measuring unit 126.

Figure 4:
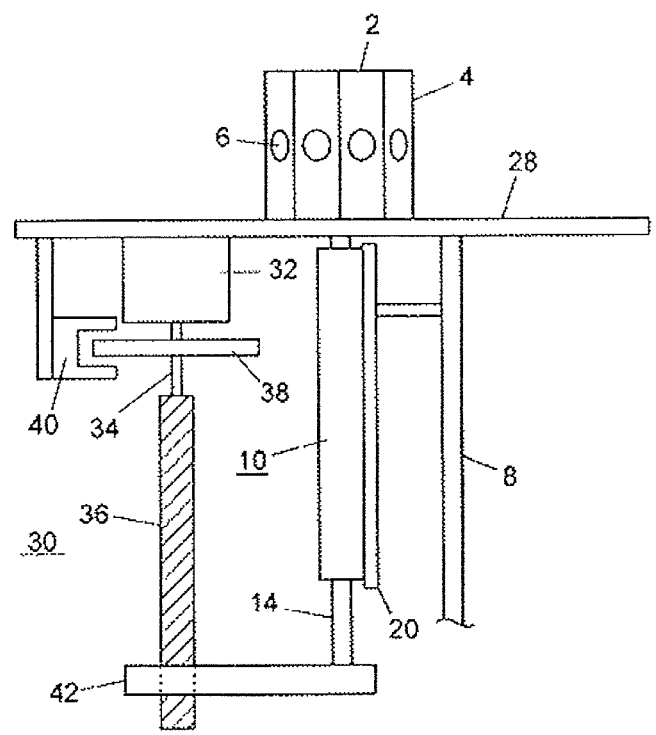
FIG. 4 is a schematic front view illustrating a specific example of a syringe driving mechanism in the TOC measurement instrument shown in FIG. 3.

FIG. 4 shows a specific example of the syringe driving mechanism 30.

The 8-port valve 2 that is a multiport valve is attached to a multiport valve support plate 28, and the syringe 10 is attached to a syringe support plate 20. The two support plates 28 and 20 are integrated by being fixed to a base plate 8, so that the relative positional relationship between the 8-port valve 2 and the syringe 10 is fixed.

The valve 2 includes eight ports 6 in a stator 4. As shown in FIG. 3, the ports 6 include at least ports that connect to the channels 110, 112, 114, and 116, respectively, and a common port that connects to an inlet/outlet port 13 of the syringe 10. A rotor (not shown in the drawings) is rotatably provided inside the stator 4. The rotor rotates while sliding with respect to the stator 4 to switch a connection between a port connected to a channel and the common port.

The syringe driving mechanism 30 that drives the syringe 10 includes a syringe support unit, the pulse motor 32, and the rotation detection mechanism. The syringe support unit includes a piston rod support body 42 that is attached to the piston rod 14, and the ball screw 36 that is screwed together with the piston rod support body 42, and moves the piston rod support body 42 by rotation of the ball screw 36 by employing the ball screw 36 as a linear feed mechanism. The ball screw 36 is attached to the rotating shaft 34 of the pulse motor 32, and the pulse motor 32 is attached to the support plate 28. As shown in FIG. 1, the coupling 38 corresponding to the rotation detection mechanism is formed in a disk shape and has the slit 39 in a radial direction thereof, and is attached to the rotating shaft 34 of the pulse motor 32 so as to rotate together with the ball screw 36. The photo sensor 40 that is combined with the coupling 38 so as to detect the position of the slit 39 of the coupling 38 is attached to the support plate 28.

Next, a syringe driving method according to this embodiment is described.

In the case of performing measurement a plurality of times using sample water that has been sucked into the syringe 10, after commencing the measurement operation, it is necessary to determine the point to start the first measurement, that is, to determine a ball screw rotation position that is the sample injection start position (zero point). A method of detecting the zero point is described below.

(1) The motor 32 is operated for 20 pulses or more and a location is detected that continuously enters a light-shielded state.

(2) Next, the motor 32 is operated for 3 pulses or more and a location is detected that continuously enters a state in which light is transmitted thereto, more specifically, a location at which the slit 39 comes to the position of the sensor 40 is detected.

(3) Subsequently, the motor 32 is operated for 20 pulses or more and a location is detected that continuously enters a light-shielded state.

The steps from (1) to (3) are performed in order, and the position of (3) is stored in the control device 50 as the zero point (measurement start position).

After the first measurement ends, the rotational position of the ball screw 36 at the measurement start time for the second measurement is set to the position of the zero point that is stored in the control device 50. At this time, if the number of rotations in the first measurement is a multiple of one rotation of the ball screw 36, it is not necessary to align the rotational position of the ball screw 36 with the zero point position at the next measurement. Measurement is repeated five times by supplying the sample water that has been sucked into the syringe 10 to the oxidative decomposition unit 118 in separate five discharges.

Thus, the flow rate of the sample water during the plurality of measurements is always the same, and variations in measurement values caused by a feed error of the ball screw 36 are reduced.

Figure 2:
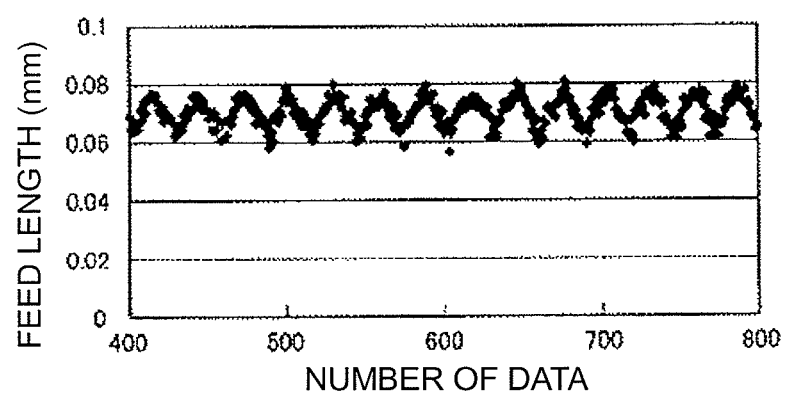
FIG. 2 is a graph illustrating a feed error of a ball screw.

A specific measurement example will now be described. As shown in FIG. 2, when sample water is discharged without executing the control of the present invention, a feed error of the ball screw 36 used in this case is a flow rate error of approximately ±10 μm as a discharge amount from the syringe, and results in a variation of approximately 20 μgC/L with respect to a detected measurement value.

If a cycle of a feed error of the ball screw is assumed to be a sine curve, when there is a deviation of 0.9 degrees (corresponds to one pulse of the pulse motor), there is a maximum error of 0.31 μgC/L.

$$20(\mu gC/L) \times \sin(0.9°) = 0.31 \, \mu gC/L$$

At this time, since the slit 39 with respect to which the photo sensor 40 senses shielding or transmission of light has a width of 0.5 mm, if it is assumed that the outside diameter of the coupling 38 is 36 mm, a moving distance on the circumference when the coupling 38 moves by an amount corresponding to one pulse is:

$$36 \times \pi/400 \text{(total number of pulses for one full rotation of the coupling)} = 0.28 \, mm$$

When the width of a slit (place at which light is sensed) forming an optical path of the photo sensor 40 is taken as 0.5 mm, the number of pulses required for the coupling 38 to move 0.5 mm is:

$$0.5/0.28 = 1.77 \text{ pulses}$$

Here, if an allowable variable error with respect to a measurement value is assumed to be 1 μgC/L, the tolerable number of variable pulses is:

$$1(\mu gC/L)/0.31(\mu gC/L) = 3.22 \text{ pulses}$$

That is, a deviation up to 3.22 pulses can be tolerated with respect to the number of pulses. Since the actual number of pulses sensed by the slit of the photo sensor 40 is 1.77 pulses, it is possible to perform control within a variable error of 1 μgC/L with respect to this slit.

Thus, when the present invention is used, since measurement errors between measurements are reduced when performing measurement a plurality of times using a single stroke from the upper end to the lower end of the ball screw 36, the reproducibility is improved by repetition. Results for repetitive reproducibility produced by the effect of the present invention are shown in Table 1.

TABLE 1

| Trial number | Average value (ppbC) | CV |
|---|---|---|
| Without ball screw feed error correction | | |
| First | 496.38 | 0.62% |
| Second | 497.28 | 1.60% |
| Third | 497.78 | 1.29% |
| Fourth | 491.30 | 1.67% |

TABLE 1-continued

| Trial number | Average value (ppbC) | CV |
|---|---|---|
| With ball screw feed error correction | | |
| First | 502.16 | 0.55% |
| Second | 507.46 | 0.70% |
| Third | 505.56 | 0.86% |
| Fourth | 503.36 | 0.44% |

The table on the upper side in Table 1 shows results for a case in which rotational control of a pulse motor according to the present invention was not performed, which corresponds to the conventional technology. In comparison therewith, the table on the lower side in Table 1 shows results for a case in which a pulse motor was controlled so as to uniformize the rotation starting positions of a ball screw in each measurement according to the present invention, and it is found that the coefficient of variation CV (standard deviation/average value) is improved.

REFERENCE SIGNS LIST

10 Syringe
11 Cylinder
12 Piston
13 Liquid inlet/outlet port
14 Piston rod
30 Syringe support unit
32 Pulse motor
36 Ball screw
38 Slit
38 Coupling
40 Photo sensor
42 Piston rod support body
50 Control device
100 Total organic carbon measurement instrument
102 Liquid feeding device
118 Oxidative decomposition unit
124 Carbon dioxide separation unit
126 Conductivity measuring unit

What is claimed is:

1. A liquid feeding device, comprising:
a syringe having a piston capable of sliding in a cylinder, and having a liquid inlet/outlet port at a distal end of the cylinder, in which a piston rod that is integrated with the piston protrudes to a proximal end side of the cylinder, the syringe performing suction and discharge of a liquid from the inlet/outlet port by causing the piston to slide through the piston rod;
a syringe support unit comprising a piston rod support body that is attached to the piston rod, and a ball screw that is screwed together with the piston rod support body, the syringe support unit using the ball screw as a linear feed mechanism to move the piston rod support body by rotation of the ball screw;
a pulse motor that causes the ball screw to rotate;
a rotation detection mechanism comprising a coupling formed in a disk shape that has a slit in a radial direction and that is attached integrally with the ball screw so as to rotate together with the ball screw, and a photo sensor that is combined with the coupling so as to detect a position of the slit of the coupling; and
a control device that controls driving of the pulse motor so as to discharge a liquid that is sucked into the syringe in a single suction process over a plurality of discharge processes, and so that rotation of the ball screw for executing each discharge process starts from an identical rotational angle position relative to the slit.

2. A total organic carbon measurement instrument, comprising:
a sample supply unit including a liquid feeding device that collects and supplies sample water;
an oxidative decomposition unit that is connected to the sample supply unit and that oxidizes organic matter contained in the sample water supplied from the sample supply unit to carbon dioxide;
a carbon dioxide separation unit that includes a sample water channel through which the sample water that has passed through the oxidative decomposition unit flows, and a measurement water channel through which measurement water comprising deionized water flows, wherein a gas permeable membrane is interposed between the sample water channel and the measurement water channel to enable transfer of carbon dioxide therethrough; and
a conductivity measuring unit that measures a conductivity of the measurement water from the carbon dioxide separation unit;
wherein a liquid feeding device according to claim 1 is used as the liquid feeding device of the sample supply unit.

3. The total organic carbon measurement instrument according to claim 2, wherein:
the sample supply unit comprises a multiport valve including at least a port connected to a channel that supplies sample water, a port connected to a channel that supplies pure water, a port connected to the oxidative decomposition unit, a port opened to the atmosphere, and a common port that is in communication with any one of the ports by switching; and
the inlet/outlet port of the syringe of the liquid feeding device is connected to the common port.

4. A method of liquid feeding using a liquid feeding apparatus including a syringe having a piston capable of sliding in a cylinder, and having a liquid inlet/outlet port at a distal end of the cylinder, in which a piston rod that is integrated with the piston protrudes to a proximal end side of the cylinder, the syringe performing suction and discharge of a liquid from the inlet/outlet port by causing the piston to slide through the piston rod; a syringe support unit comprising a piston rod support body that is attached to the piston rod, and a ball screw that is screwed together with the piston rod support body, the syringe support unit using the ball screw as a linear feed mechanism to move the piston rod support body by rotation of the ball screw; a pulse motor that causes the ball screw to rotate; a rotation detection mechanism comprising a coupling formed in a disk shape that has a slit in a radial direction and that is attached integrally with the ball screw so as to rotate together with the ball screw, and a photo sensor that is combined with the coupling so as to detect a position of the slit of the coupling, the method comprising:
controlling driving of the pulse motor so as to discharge a liquid that is sucked into the syringe in a single suction process over a plurality of discharge processes, and so that rotation of the ball screw for executing each discharge process starts from an identical rotational angle position relative to the slit.

* * * * *